(12) United States Patent
Shaffer

(10) Patent No.: US 10,379,082 B2
(45) Date of Patent: Aug. 13, 2019

(54) SYSTEM FOR MONITORING MACHINE FLUIDS BY MEASURING FLUCTUATIONS IN A MAGNETIC FIELD

(71) Applicant: CATERPILLAR INC., Peoria, IL (US)

(72) Inventor: Kristopher Eric Shaffer, Dunlap, IL (US)

(73) Assignee: Caterpillar Inc., Deerfield, IL (US)

( * ) Notice: Subject to any disclaimer, the term of this patent is extended or adjusted under 35 U.S.C. 154(b) by 281 days.

(21) Appl. No.: 15/380,401

(22) Filed: Dec. 15, 2016

(65) Prior Publication Data

US 2018/0172636 A1   Jun. 21, 2018

(51) Int. Cl.

| | |
|---|---|
| G01N 27/74 | (2006.01) |
| G01N 33/28 | (2006.01) |
| F01M 1/02 | (2006.01) |
| F01M 11/10 | (2006.01) |
| F04C 2/14 | (2006.01) |
| F04C 2/344 | (2006.01) |
| F04C 28/28 | (2006.01) |
| F04C 18/08 | (2006.01) |
| F04C 18/18 | (2006.01) |
| F04C 18/344 | (2006.01) |

(52) U.S. Cl.
CPC .............. *G01N 27/74* (2013.01); *F01M 1/02* (2013.01); *F01M 11/10* (2013.01); *F04C 2/14* (2013.01); *F04C 2/344* (2013.01); *F04C 18/084* (2013.01); *F04C 18/18* (2013.01); *F04C 18/344* (2013.01); *F04C 28/28* (2013.01); *G01N 33/2888* (2013.01); *F01M 2001/0238* (2013.01); *F01M 2011/144* (2013.01); *F04C 2240/30* (2013.01); *F04C 2240/81* (2013.01)

(58) Field of Classification Search
CPC ...................................................... G01N 27/74
USPC .......................... 73/114.41, 114.55, 114.56
See application file for complete search history.

(56) References Cited

U.S. PATENT DOCUMENTS

| | | | | |
|---|---|---|---|---|
| 5,614,830 | A * | 3/1997 | Dickert | G01N 15/0656 |
| | | | | 210/695 |
| 6,571,626 | B1 * | 6/2003 | Herford | G01F 23/74 |
| | | | | 73/290 R |
| 6,789,442 | B2 | 9/2004 | Forch | |
| 7,043,967 | B2 | 5/2006 | Kauffman et al. | |
| 7,151,383 | B2 | 12/2006 | Itomi | |
| 7,868,616 | B2 | 1/2011 | White et al. | |
| 8,480,815 | B2 * | 7/2013 | Wang | H01F 1/0572 |
| | | | | 148/101 |
| 2009/0293637 | A1 * | 12/2009 | Ertler | G01F 3/10 |
| | | | | 73/861.77 |
| 2010/0263454 | A1 * | 10/2010 | Araseki | G01F 1/582 |
| | | | | 73/861.11 |

(Continued)

FOREIGN PATENT DOCUMENTS

DE   10 2006 007 554 A1   8/2007

*Primary Examiner* — Eric S. McCall
(74) *Attorney, Agent, or Firm* — Finnegan, Henderson, Farabow, Garrett & Dunner, LLP

(57) ABSTRACT

A system for monitoring machine fluids is provided. The system includes a fluid handling unit configured to pump the fluid and the fluid handling unit includes at least one fluid handling element. A magnetic material on the at least one fluid handling element is configured to generate a magnetic field. A sensing element located within the magnetic field is configured to measure fluctuations in the magnetic field.

16 Claims, 3 Drawing Sheets

(56) References Cited

U.S. PATENT DOCUMENTS

| | | | |
|---|---|---|---|
| 2013/0199286 A1* | 8/2013 | Gao | E21B 49/081 |
| | | | 73/152.27 |
| 2014/0116131 A1* | 5/2014 | Forgue | G01F 23/38 |
| | | | 73/313 |
| 2014/0147305 A1* | 5/2014 | Johansson | A47J 31/402 |
| | | | 417/410.1 |
| 2014/0188404 A1 | 7/2014 | Von Herzen et al. | |
| 2014/0263063 A1* | 9/2014 | Jones | A61M 1/16 |
| | | | 210/647 |
| 2014/0366641 A1* | 12/2014 | Jedema | G01F 25/0007 |
| | | | 73/861.12 |
| 2015/0118077 A1* | 4/2015 | Humburg | F04B 17/003 |
| | | | 417/322 |
| 2016/0094099 A1* | 3/2016 | Moritz | H02K 1/274 |
| | | | 310/156.08 |
| 2017/0261866 A1* | 9/2017 | Cadee | F28D 15/02 |
| 2018/0269751 A1* | 9/2018 | Foerch | F04B 49/06 |

\* cited by examiner

SYSTEM FOR MONITORING MACHINE FLUIDS BY MEASURING FLUCTUATIONS IN A MAGNETIC FIELD

TECHNICAL FIELD

The present disclosure relates generally to machine fluids and, more particularly, to a system for monitoring machine fluids.

BACKGROUND

Machines, such as excavating machines, material handling machines, vehicles, and generators, generally include various components and/or systems that require a fluid for proper operation. The type of fluid may vary with the particular component or system. For example, engines, such as gasoline engines, diesel engines, and gaseous-fuel powered engines, may require a lubricating fluid such as engine oil. Typically, engine oil or other system fluids and lubricants may be circulated within an associated component or system by a pump, such as a gear pump.

Engine oil or other system fluids may be exposed to wide variations in temperature including high heat, for example from engine operation. During machine operation, lubricating fluids may become contaminated by various substances, such as metallic particles from mechanical wear or the addition to the fluid of an incorrect additive package. In addition, engine oil may experience acid buildup, breakdown, and/or shearing of molecules and suffer a loss of optimum lubricating properties. All of these factors may lead to failure of a lubricating or other fluid to optimally achieve its primary purpose, such as lubricating and extending the life of machine components and systems. As a result, increased maintenance time and costs and even machine system failure may result.

Lubricating fluids such as engine oil may be monitored manually via a so-called dip stick. Other machine fluids may be checked by visual inspection. This may allow, in addition to determination of the level of fluid present, a rough determination of contamination. A more accurate determination may be made by taking a sample for external analysis of the level and type of contaminants or the degree of breakdown of fluid properties. In addition, some systems may include sensors capable of sensing certain contaminants in a fluid.

The use of manual determination of the quality of fluids relies on a technician or machine operator making what may at best be a rough guess. Taking samples for laboratory analysis may be unduly time consuming and still may rely on employees scheduling the sampling process. Where an incorrect additive package has been introduced, damage may already have been done by the time a sample has been taken. Currently available sensors may give only a partial analysis for a certain contaminant. It would be both beneficial and desirable to be able to remotely monitor a range of contaminants and/or characteristics of fluids, such as engine oil, hydraulic fluid, etc., to obtain continuous or closely intermittent data on the quality of the fluid.

One fluid sensing system is disclosed in U.S. Patent Application Publication No. 2014/0188404 naming Von Herzen et al. as inventors and published on Jul. 3, 2014 ("the '404 publication"). Specifically, the '404 publication discloses a fluid sensing system including multiple sensors submerged in the fluid to be monitored. An exemplary embodiment disclosed in the '404 publication includes multiple sensing components mounted on a bolt, which may be the bolt typically employed as a drain plug in an oil pan.

While the system disclosed in the '404 publication may be suitable for monitoring the character of fluids, it may be unduly complex and too expensive for general use. The system includes a number of sensitive components which must endure high temperature while continuing to function accurately. Furthermore, the system of the '404 publication may not be suitable for the harsh environment and operating conditions experienced by heavy equipment such as excavators and mining machines.

The disclosed system for monitoring machine fluids is directed to overcoming one or more of the problems set forth above.

SUMMARY

According to one exemplary aspect, a fluid monitoring system may include a fluid handling unit configured to handle the fluid. The fluid handling unit may include at least one fluid handling element. A magnetic material may be located on the at least one fluid handling element and may be configured to generate a magnetic field. A sensing element may be located within the magnetic field and may be configured to measure fluctuations in the magnetic field.

According to another exemplary aspect, the present disclosure is directed to a system for monitoring a lubricant in a machine for contamination and deterioration. The system may include a pump including a plurality of pumping elements. The system also may include a magnetic material on the pumping elements generating a magnetic field. The system also may include a sensing element adjacent the pump and within the magnetic field. The sensing element may be configured to detect fluctuations in the magnetic field. The magnetic field may fluctuate responsive to changes in a characteristic of the lubricant, and the sensing element may be calibrated to generate signals corresponding to the changes in the characteristic.

According to yet another exemplary aspect, the present disclosure is directed to a system for monitoring the useful life of engine oil. The system may include an internal combustion engine. The system also may include an oil pump configured to pump engine oil for lubricating the internal combustion engine. The system also may include a plurality of oil moving elements on the oil pump. The system also may include a magnetic material coating on the oil moving elements and generating a magnetic field. The system also may include a sensing element configured to measure fluctuations in the magnetic field. The system also may include a communication device configured to transmit signals corresponding to and indicative of fluctuations in the magnetic field. The system also may include a receiver for receiving the signals from the communication element. The system also may include a controller for processing the signals. The system also may include a display for displaying visual data representative of the fluctuations in the magnetic field.

DETAILED DESCRIPTION

Figure 1:
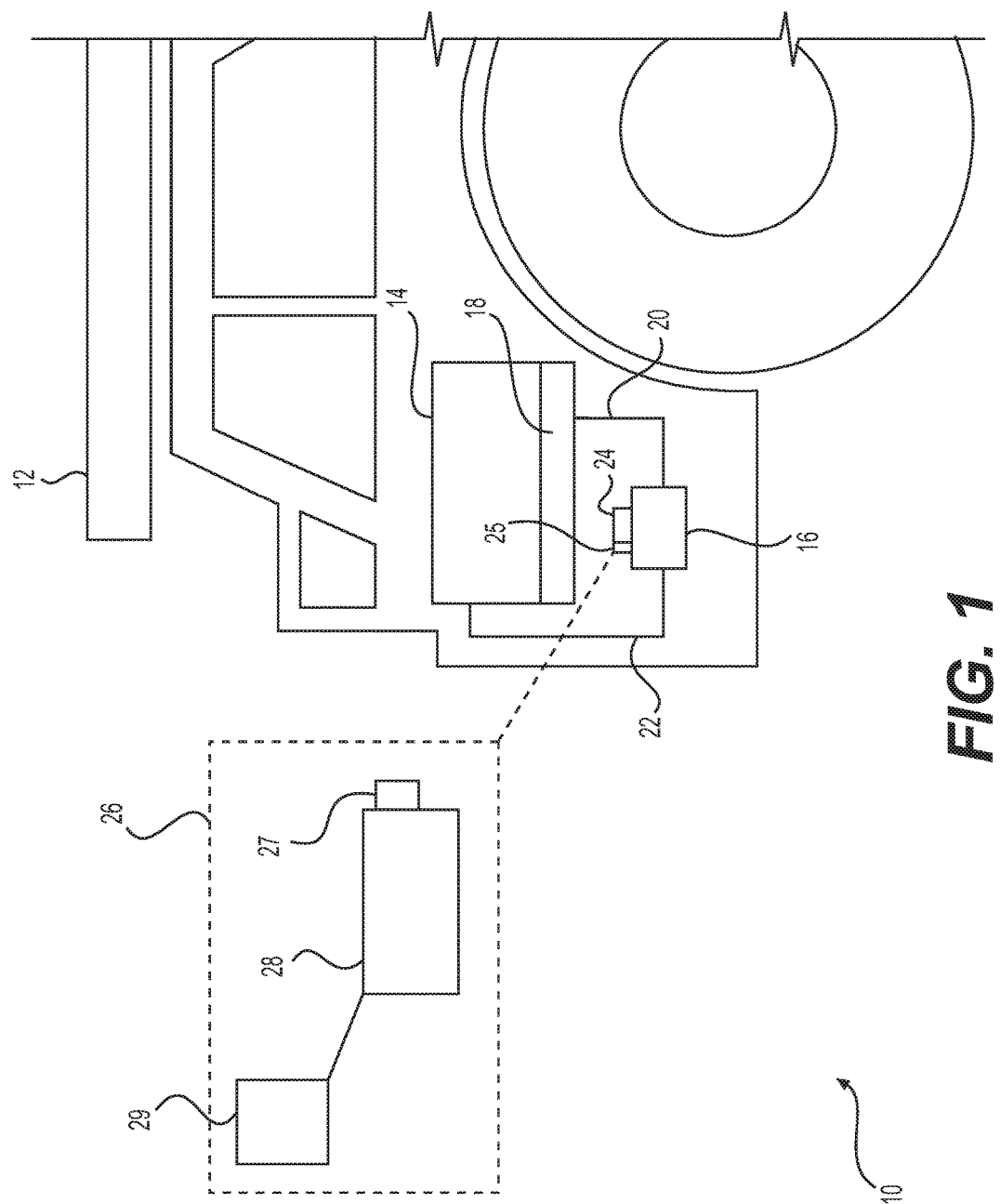
FIG. 1 schematically illustrates an exemplary system for monitoring machine fluids according to disclosed embodiments.

FIG. 1 illustrates a fluid monitoring system 10 implemented for a machine 12. Machine 12 is illustrated as a mining truck or haulage machine (with only the frontal portion being shown), but it will be understood that machine 12 may be any type of machine that includes a fluid system which may benefit from a monitoring system that is capable of assessing contamination and/or deterioration of the fluid. For example, it is contemplated that the disclosed fluid monitoring system 10 may be employed with various types of vehicles, mining machines, excavating machines, material handling machine, generators, etc.

In the embodiment illustrated in FIG. 1, the fluid monitoring system 10 is employed in connection with the engine 14 of machine 12. Engine 14 may be an internal combustion engine, such as a diesel or gasoline engine, that requires a lubricant such as engine oil for lubricating bearings and other engine components. In order to ensure circulation of engine oil to engine 14, a pump 16 may be employed. Pump 16 may be any of various available types of pumps, for example, an internal or external gear pump, a gerotor, a vane pump, etc.

Pump 16 may be located relative to engine 14 so as to readily draw engine oil from a reservoir 18 which typically may be a sump at the lower portion of engine 14 as schematically illustrated in FIG. 1. Pump 16 may withdraw engine oil from reservoir 18 through a pump intake line 20 and force the engine oil back into engine 14 under pressure via a line 22 in order to lubricate the bearings and other components (not shown) within engine 14. While not illustrated, various conventional oil filters, oil coolers, and/or other components may be disposed within pump intake line 20 and/or line 22, or otherwise adjacent pump 16. While reservoir 18 is illustrated within engine 14, it also is contemplated that reservoir 18 could be separate from engine 14. Pump 16 may be mounted outside of engine 14, for example adjacent a lower portion of engine 14 and as illustrated, or alternatively, pump 16 may be mounted submerged within reservoir 18.

As described in subsequent embodiments, pump 16 may be configured to generate a magnetic field. Fluid monitoring system 10 may include a sensing element 24 mounted on or adjacent pump 16, within the generated magnetic field generated by pump 16, and configured to measure or detect fluctuations in the magnetic field and transmit signals, for example via a communication device 25, to a station 26 including a receiver 27 where received signals may be processed by a controller 28. The received signals may be translated to visual data on display 29. Station 26 may be an on-board station or it may be a remote station. Signals may be transmitted from on-board machine 12 to a remote monitoring station via any known expedient such as, for example, WiFi, cellular, satellite, bluetooth, ground line, etc. The remote monitoring station may be any of a fixed or mobile station and may include a smart phone application, a personal or commercial cloud based application, etc.

Figure 2:
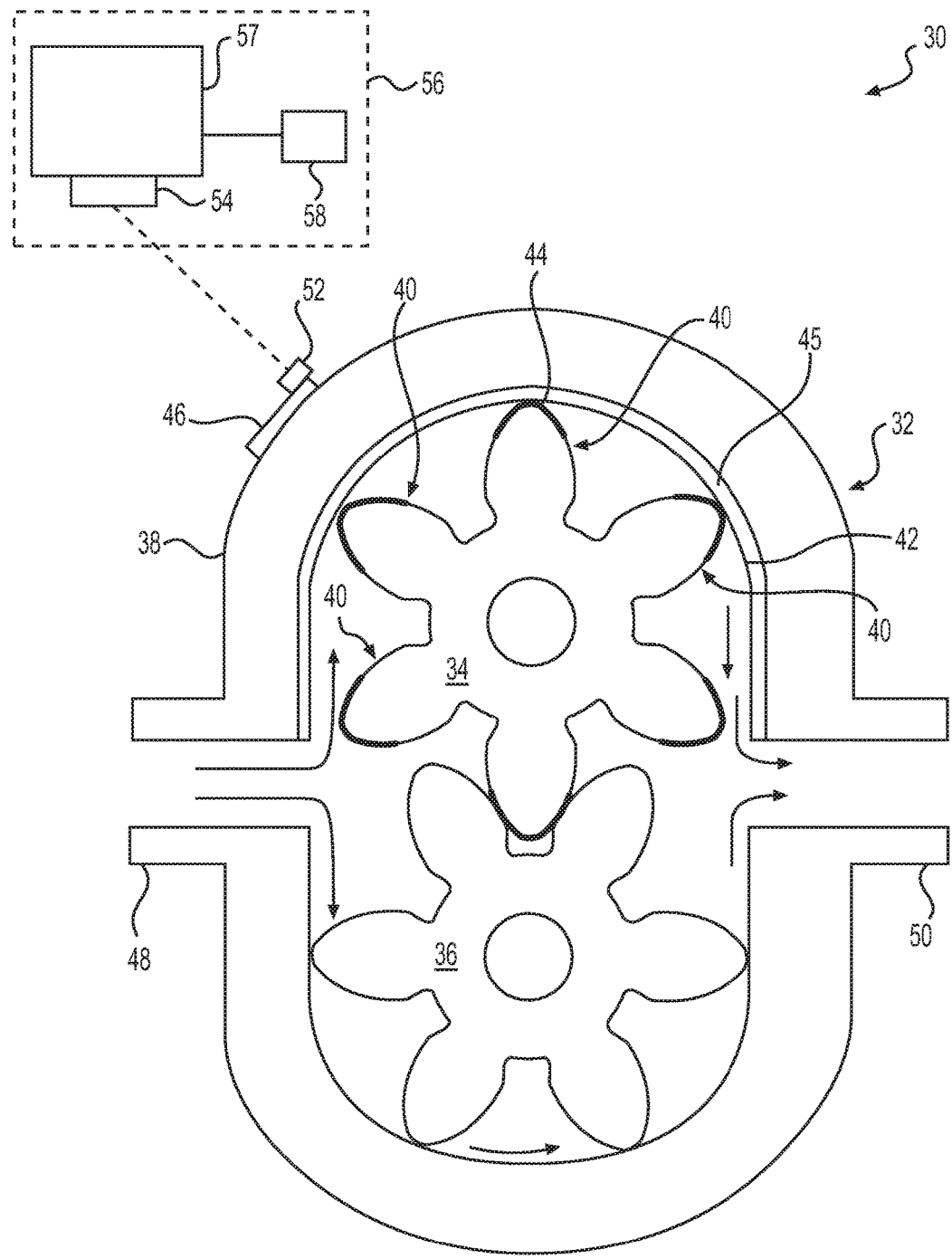
FIG. 2 schematically illustrates an exemplary system for monitoring machine fluids according to disclosed embodiments and an exemplary pump which may be employed in connection with disclosed embodiments.

Referring now to FIG. 2, an embodiment of a fluid monitoring system 30 is schematically illustrated. Fluid monitoring system 30 may include a gear pump 32. Gear pump 32 may take various well know forms, and is here illustrated as including two meshing gears—gear 34 and gear 36. One of gears 34 and 36 may be a driving gear, while the other of gears 34 and 36 may be a driven gear. Gear pump 32 may include a housing 38 which encloses the two meshing gears 34 and 36. Gears 34 and 36 may include pumping elements 40, which in the embodiment of gear pump 32, may be the teeth of gears 34 and 36.

At least one of gears 34 and 36 may include a magnetic material 44 located on at least one of pumping elements 40 and configured to generate a magnetic field. In the embodiment illustrated in FIG. 2, magnetic material 44 is illustrated as being located on each pumping element 40 of gear 34. It is contemplated that magnetic material 44 could be located on only some of the pumping elements of gear 34, for example on alternate pumping elements. It also is contemplated that magnetic material 44 could be located on one or more pumping elements of both gears 34 and 36. The magnetic material 44 may take various forms and may be included on a portion or on the entire surface area of a pumping element 40. In the embodiment of FIG. 2, magnetic material 44 is illustrated as being on the distal tips of the teeth or pumping elements 40. Magnetic material 44 may be a neodymium magnet formed, for example, as an alloy of neodymium, iron, and boron. Other magnetic materials including other rare earth magnetic materials are contemplated.

An interior wall 42 of housing 38 also may be suitably provided with a magnetic material 45 similar to magnetic material 44. For example, Magnetic material 45 may be a coating of a neodymium or other rare earth alloy that has been applied to interior wall 42, for example by a hot dip or other coating process. Magnetic material 45 alternatively may be an insert or a laminate that has been suitably applied to the surface of interior wall 42. In some situations, for example where it is contemplated that pumping elements 40 may make contact with interior wall 42, a layer of a suitable non-conductive insulating material (e.g., polymeric or ceramic material) may be applied over magnetic material 45 to prevent contact between magnetic material 45 and pumping elements 40. It should readily be understood that the thicknesses shown for magnetic material 45 is not necessarily to scale in order to aid understanding, and that the thicknesses may vary depending on various factors including pump size, for example.

The presence of magnetic material 44 on one or more pumping elements of gear 34 and on pump housing 38 will generate a magnetic field that extends to an area around the magnetic material 44 and 45. A sensing element 46 may be located within the magnetic field. In the embodiment illustrated in FIG. 2, sensing element 46 is illustrated as being located adjacent gear pump 32 and mounted on housing 38. While sensing element 46 is illustrated in this embodiment as mounted on housing 38, it should be understood that it is contemplated that sensing element 46 need not necessarily be mounted on housing 38. Sensing element 46 may be a magnetic flux sensor, e.g., a magnetometer) configured to respond to and detect and measure fluctuations in the magnetic field generated by magnetic material 44. For example, sensing element 46 may be a Hall effect sensor capable of translating fluctuations in the magnetic field to changes in voltage. However, various sensing elements may be employed that are capable of detecting fluctuations in a magnetic field generated by the magnets. The particular sensing element may be selected from known sensing elements based on the sensitivity level required for a given fluid handling system. For example, other sensors that may be employed include various search coils, inductive sensors, SQUID sensors, etc. The mounting location of sensing element 46 may vary as long as it is so positioned as to respond to and detect and measure the fluctuations in the generated magnetic field.

Gear pump 32 may be employed in a fluid circulating system of a machine, such as the system described in connection with FIG. 1 for circulating engine oil within engine 14 of machine 12. Gear pump 32 also may be employed in other types of fluid circulating systems such as hydraulic systems of various types. For example, contemplated fluid circulating systems may include hydraulic coolant systems, hydraulic motor systems, hydraulic pump systems, or any other fluid handling systems. Housing 38 may include an inlet 48 for fluid entering gear pump 32, and an outlet 50 for fluid leaving gear pump 32 and being pumped through the system or component receiving the fluid, for example the system or component being lubricated. As fluid moves through gear pump 32, changes in the character of the fluid may have an effect on the magnetic field being generated by magnetic material 44. In other words, as the fluid becomes contaminated with metallic particles (due, for example, to engine wear), becomes more acidic (typical of lubricating fluid in diesel engines), becomes contaminated with an incorrect additive package (an eventuality that sometimes inadvertently occurs), and/or otherwise changes in its physical and/or chemical characteristics, the magnetic field may respond with fluctuations.

Fluctuations in the magnetic field generated by magnetic materials 44 and 45 may be sensed and measured by sensing element 46. Sensing element 46 may include a communication device 52 configured to transmit signals corresponding to and indicative of fluctuations in the magnetic field that are sensed by sensing element 46. Signals from communication device 52 may be received by one or more receivers 54 at one or more stations 56. Station 56 typically may be at a location remote from any machine with which system 30 is associated. However, it is contemplated that station 56 also could include an operator station on any machine with which system 30 is associated. Once received by receiver 54, signals transmitted from communication device 52 may be processed by controller 57, converted to visual data representative of the fluctuations in the magnetic field, and displayed for analysis by personnel, for example via a suitable display 58. Transmission of signals may be by way of WiFi, cellular, satellite, bluetooth, ground line, or any other suitable transmission expedient.

Figure 3:
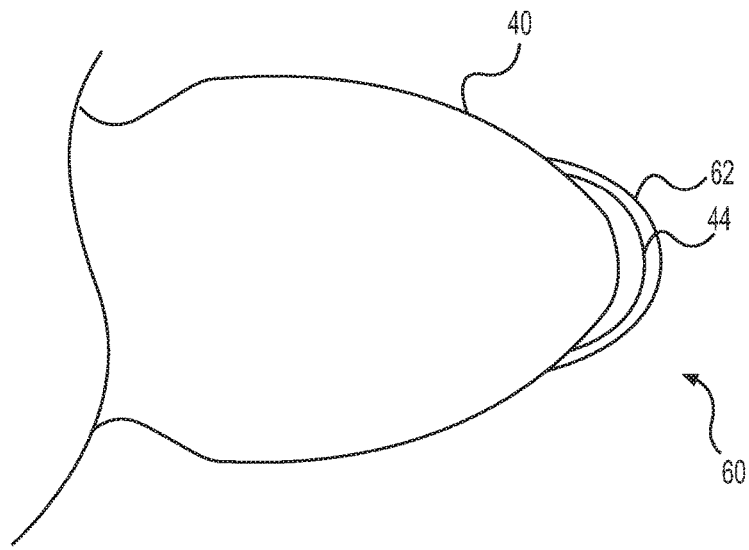
FIG. 3 schematically illustrates a pumping element of the pump illustrated in FIG. 2 and modified according to disclosed embodiments.

FIG. 3 is a schematic detail of one pumping element 40 (one gear tooth) of gear pump 32 illustrated in FIG. 2. FIG. 3 illustrates magnetic material 44 generally at the distal tip 60 of pumping element 40. Magnetic material 44 may be a coating of a neodymium or other rare earth alloy that has been applied to pumping element 40, for example by a hot dip or other coating process. Magnetic material 44 alternatively may be an insert that has been inset into a prepared groove in pumping element 40 or a laminate that has been adhered to the surface of pumping element 40. In some situations, for example where it is contemplated that pumping elements 40 may make contact with a housing wall, a layer of a suitable non-conductive insulating material 62 (e.g., polymeric or ceramic material) may be applied over magnetic material 44 to prevent contact between magnetic material 44 and an inner surface of the pump housing, such as housing 38 illustrated in FIG. 2. In addition, as described in connection with FIG. 2, insulating material may be applied to a pump housing wall itself where contact with magnetic material 44 may be contemplated. It should readily be understood that the thicknesses shown for magnetic material 44 and insulating material 62 in FIG. 3 are not necessarily to scale in order to aid understanding, and that the thicknesses may vary depending on various factors including pump size, for example.

Figure 4:
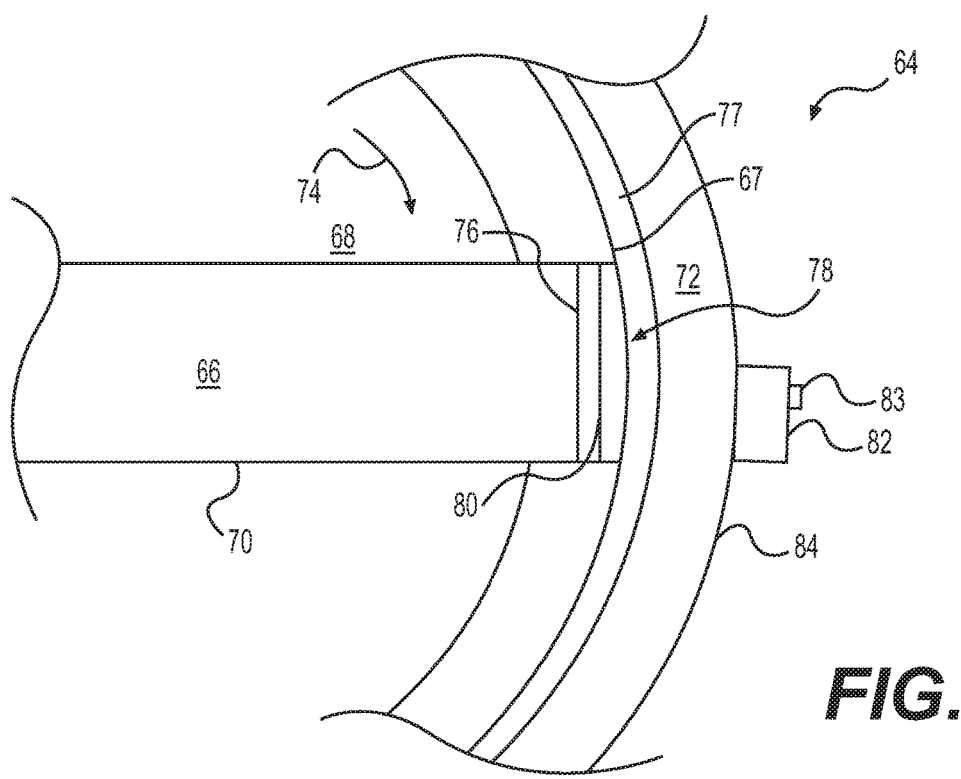
FIG. 4 schematically illustrates a portion of another exemplary pump according to disclosed embodiments.

While FIG. 2 relates to an embodiment in connection with a gear pump 32, embodiments are contemplated involving other types of pumps. For example, FIG. 4 shows an otherwise conventional vane pump 64 wherein the vanes 66 have been modified in accordance with an embodiment of the disclosure. Only a portion of the vane pump 64 has been illustrated in FIG. 4. As well known in the art, vane pumps (also known as sliding vane pumps) include an eccentric rotor 68 and a plurality of vanes 66 (only one of which is illustrated in FIG. 4) moving relative to rotor 68 (e.g., sliding in a slot 70) as rotor 68 rotates. Vanes 66 may be characterized as the pumping elements that move fluid being pumped in the direction of rotation of arrow 74 (although rotation could be in either direction).

In accordance with an embodiment of the disclosure, vane pump 64 has been modified by including a magnetic material 76 at the distal tip 78 of vane (pumping element) 66. An interior surface 67 of vane pump 64 also may include a layer of magnetic material 77 (e.g., as a coating, an insert, or a laminate). As is common for vane pumps in general, vane 66 may make direct contact with housing 72 as rotor 68 rotates and fluid is being pumped. In such a situation, magnetic materials 76 and 77 may be protected from contact with housing 72 by non-conductive insulating material 80, illustrated on magnetic material 76, and a similar non-conductive insulating material on magnetic material 77. For example, the insulating material may be polymeric or ceramic material applied over (e.g., coated, laminated, etc.) magnetic materials 76 and/or 77 so as to be located at the distal tip 78 and/or on interior surface 77 ensuring that direct contact between magnetic materials 76 and 77 and housing 72 does not occur.

In accordance with the disclosure, magnetic materials 76 and 77 (e.g., a neodymium alloy) may generate a magnetic field. Within the magnetic field, sensing element 82 may be suitably located, for example mounted on an external surface 84 of housing 72. While sensing element 82 is shown mounted on external surface 84 of housing 72, it is contemplated that sensing element 82 may be located within the magnetic field but mounted otherwise than on housing 72. During operation of vane pump 64 and as fluid is pumped throughout the system being serviced by vane pump 64, contamination and/or deterioration of the fluid being pumped may cause fluctuations in the magnetic field. Sensing element 82 may be a magnetic flux sensor, for example, a Hall effect sensor, configured to detect fluctuations in the magnetic field and, via a suitable communication device 83, for example, send signals indicative of those fluctuations to be received at another location, for example a remote location (for example via WiFi, cellular, satellite, bluetooth, ground line, or any other suitable transmission expedient), substantially as described in connection with the previously described embodiments of FIGS. 1 and 2. The particular sensing element employed may be selected from known sensing elements based on the sensitivity level required for a given fluid handling system. For example, other sensors that may be employed include various search coils, inductive sensors, SQUID sensors, etc.

INDUSTRIAL APPLICABILITY

Disclosed embodiments of the system for monitoring machine fluids may be applicable to various machines, such as excavators, material handling machines, mining machines, on-road and off-road vehicles and machines, generators, etc., that include engines, transmissions, or other systems that require lubricating or other system fluids. In order to facilitate determination of aspects of such machine fluids that may correlate to contamination and/or deterioration of the fluid, presently disclosed embodiments of the system may be implemented with the pumping units typically employed for circulating the lubricating fluid. One example of a system which may benefit from implementation of disclosed embodiments is the oil pumping system for engine oil in internal combustion engines.

With disclosed embodiments, characteristics of engine oil that may be correlated with engine wear, oil deterioration, introduction of an incorrect additive package, etc., may be monitored continuously. Results of monitoring may be displayed to a machine operator or other personnel at nearby or remote locations. The display may be configured to give a visible indication of changes in one or more characteristics of the engine oil. This may yield useful data for determining when service is necessary, such as an oil change, thereby potentially extending engine and machine life. In the case of inadvertent introduction of an incorrect additive package, which may either not accomplish the intended result of the correct additive package or, in a worse case, actually harm machine components, an immediate change in magnetic flux may be detected and indicated to personnel so that machine operation can be halted while the matter is corrected and before any damage is done.

Advantageously, use is made of neodymium magnets. Neodymium magnets are both strong and generally available. Placement of the magnets on the pumping elements of the pump enables their installation at manufacture of the pump. In case the pump is replaced, the replacement pump also may be manufactured to include the magnets as an integral part. Various sensing elements may be employed that are capable of detecting fluctuations in a magnetic field generated by the magnets. The particular sensing element may be selected from known sensing elements based on the sensitivity level required for a given fluid handling system. For example, readily available magnetometers such as Hall effect sensors configured to respond to magnetic field fluctuations by a change in voltage advantageously may be employed. Other more sensitive magnetometers that may be employed where more sensitivity is necessary or desirable may include various search coils, inductive sensors, SQUID sensors, etc.

It is within the scope of this disclosure to use different types of pumps with the disclosed fluid monitoring system. For example, in addition to the type of gear pump 32 illustrated in FIG. 2, the pump could be a gear pump generally well known as a gerotor which includes two meshing gears with one of the gears being an internal gear and the other gear being an external gear mounted within and eccentrically relative to the internal gear. The projections or teeth of one of the gears, either the internal gear or the external gear, may be provided with the magnetic material to generate the magnetic field. The application of the magnetic material for a gerotor may be similar to that illustrated in FIGS. 2 and 3, for example.

Advantageously, the disclosed embodiments of the system for monitoring machine fluids may be applicable to motors as well as pumps. Identical fluid handling units may operate both a pumps and as motors depending on whether the fluid is being pumped by the unit or the fluid is driving the unit. Accordingly, it is within the scope of this disclosure and contemplated that fluid characteristics, such as contamination, may be measured in fluid handling systems that include either pumps or motors or both pumps and motors. For example, it is contemplated that hydraulic motors of various types employed in machines to drive wheels or other traction devices or other machine components may employ the disclosed system for monitoring machine fluids.

In addition, the pump could be a generally well known vane pump in which sliding vanes within a rotor cooperate with a housing enclosing the rotor. The magnetic material to generate the magnetic field could be provided on the sliding vanes. In order to inhibit noise or interference with the magnetic field, the sliding vanes may be insulated with a non-conductive material. It is contemplated that fluid monitoring systems according to this disclosure could be employed in systems with pumps other than those described in the disclosed embodiments.

It will be apparent to those skilled in the art that various modifications and variations can be made to the disclosed system for monitoring machine fluids. Other embodiments will be apparent to those skilled in the art from consideration of the specification and practice using the disclosed system for monitoring machine fluids. It is intended that the specification and examples be considered as exemplary only, with a true scope being indicated by the following claims and their equivalents.

What is claimed is:

1. A fluid monitoring system comprising:
   a fluid handling unit configured to handle the fluid and including at least one fluid handling element, wherein the fluid handling unit is a pump and the at least one fluid handling element is a pumping element, and wherein the pump includes a housing for the at least one pumping element, and the sensing element is a magnetometer located on the housing;
   a magnetic material located on the at least one fluid handling element and configured to generate a magnetic field, wherein the magnetic material is an alloy including neodymium; and
   a sensing element located within the magnetic field and configured to measure fluctuations in the magnetic field.

2. The fluid monitoring system of claim 1, wherein the magnetometer is configured to generate signals corresponding to measured fluctuations in the magnetic field and transmit the generated signals to a receiver.

3. The fluid monitoring system of claim 1, wherein the pump is a gear pump including two meshing gears, and the at least one pumping element includes a plurality of teeth of the two meshing gears, and the teeth of at least one of the two meshing gears include the magnetic material.

4. The fluid monitoring system of claim 3, wherein the magnetic material is an alloy including neodymium and is one of a coating, an insert, and a laminate on distal tips of the teeth of the at least one of the two meshing gears.

5. The fluid monitoring system of claim 4, further including a magnetic material on an interior surface of the housing.

6. A system for monitoring a lubricant in a machine for contamination and deterioration, comprising:
   a pump including a plurality of pumping elements;
   a magnetic material on the pumping elements and generating a magnetic field; and
   a sensing element adjacent the pump and within the magnetic field, the sensing element configured to detect fluctuations in the magnetic field;
   wherein the magnetic field fluctuates responsive to changes in a characteristic of the lubricant, and the sensing element is calibrated to generate signals corresponding to the changes in the characteristic.

7. The system of claim 6, wherein the pump is a vane pump including a housing, and the plurality of pumping elements are vanes, and wherein the magnetic material is a neodymium alloy at distal tips of the plurality of pumping elements, and further including a neodymium alloy on an interior surface of the housing, a non-conductive insulating material over the neodymium alloy at the distal tips of the vanes, and a non-conductive insulating material over the neodymium alloy on the interior surface of the housing.

8. The system of claim 6, wherein the pump is a gear pump including a housing enclosing two meshing gears, and the sensing element is mounted on the housing.

9. The system of claim 8, wherein the signals are transmitted to a receiving location including a display configured to give a visible indication of the changes in the characteristic.

10. The system of claim 9, wherein the changes in the characteristic of the lubricant is caused by one or more of lubricant deterioration, machine wear, and introduction of an incorrect additive package to the lubricant.

11. The system of claim 10, wherein the sensing element is a magnetometer and the magnetic material is a neodymium alloy on distal tips of a plurality of teeth of one of the gears.

12. A system for monitoring the useful life of engine oil, comprising:
an internal combustion engine:
an oil pump configured to pump engine oil for lubricating the internal combustion engine;
a plurality of oil moving elements on the oil pump;
a magnetic material coating located on the oil moving elements and generating a magnetic field; and
a sensing element configured to measure fluctuations in the magnetic field;
a communication device configured to transmit signals corresponding to and indicative of fluctuations in the magnetic field;
a receiver for receiving the signals from the communication element;
a controller for processing the signals; and
a display for displaying visual data representative of the fluctuations in the magnetic field.

13. The system of claim 12, wherein the plurality of oil moving elements are within a housing and the magnetic material coating located on the plurality of oil moving elements is an alloy including neodymium, and the sensing element is located on an exterior surface of the housing.

14. The system of claim 13, wherein an interior surface of the housing includes a layer of an alloy including neodymium, and at least one of the housing and the plurality of oil moving elements includes a non-conductive insulating material configured to inhibit direct contact between the plurality of oil moving elements and the housing.

15. The system of claim 13, wherein the oil pump is a gear pump including two meshing gears and the plurality of oil moving elements are teeth of the two meshing gears.

16. The system of claim 15, wherein the magnetic material coating is on distal tips of the teeth of one of the two meshing gears, and the sensing element located on the exterior surface of the housing is one of a Hall effect sensor, a search coil, an inductive sensor, and a SQUID sensor.

* * * * *